United States Patent
Harrison, Sr.

(10) Patent No.: US 10,799,386 B1
(45) Date of Patent: Oct. 13, 2020

(54) EXTERNAL CATHETER

(71) Applicant: Robert L. Harrison, Sr., Blacksburg, VA (US)

(72) Inventor: Robert L. Harrison, Sr., Blacksburg, VA (US)

( * ) Notice: Subject to any disclaimer, the term of this patent is extended or adjusted under 35 U.S.C. 154(b) by 0 days.

(21) Appl. No.: 16/288,862

(22) Filed: Feb. 28, 2019

Related U.S. Application Data

(63) Continuation-in-part of application No. 15/594,592, filed on May 13, 2017.

(51) Int. Cl.
| | |
|---|---|
| *A61M 5/32* | (2006.01) |
| *A61F 5/44* | (2006.01) |
| *A61F 5/453* | (2006.01) |
| *A61F 5/441* | (2006.01) |
| *A61M 1/00* | (2006.01) |
| *A61M 27/00* | (2006.01) |

(52) U.S. Cl.
CPC .............. *A61F 5/453* (2013.01); *A61F 5/441* (2013.01); *A61F 5/4408* (2013.01)

(58) Field of Classification Search
CPC .......... A61M 5/32; A61M 1/00; A61M 27/00; A61F 5/44; A61B 19/00
See application file for complete search history.

(56) References Cited

U.S. PATENT DOCUMENTS

| | | | |
|---|---|---|---|
| 4,022,213 A | 5/1977 | Stein | |
| 4,846,816 A * | 7/1989 | Manfredi | A61F 5/4405 604/323 |
| 5,618,277 A | 4/1997 | Goulter | |
| 2002/0193763 A1* | 12/2002 | Kulikov | A61F 5/453 604/353 |
| 2004/0176746 A1 | 9/2004 | Forral | |
| 2006/0015082 A1 | 1/2006 | Pearson et al. | |
| 2012/0165768 A1 | 6/2012 | Sekiyama et al. | |
| 2013/0338617 A1 | 12/2013 | Newton, Jr. | |
| 2015/0320583 A1 | 11/2015 | Harvie | |

FOREIGN PATENT DOCUMENTS

| | | |
|---|---|---|
| CN | 105287084 A * | 10/2015 |
| WO | 97/14353 | 4/1997 |

* cited by examiner

*Primary Examiner* — Tatyana Zalukaeva
*Assistant Examiner* — Ilya Y Treyger
(74) *Attorney, Agent, or Firm* — NK Patent Law

(57) ABSTRACT

A harness has a harness body, a belt strap, two leg straps, a small opening to slidably accommodate an aeration tube, and a larger opening to accommodate a catheter sleeve. The catheter sleeve has a length of cylindrical body which has a tapered end and a flexible end that extends though the harness body about a half inch. The one end of the aeration tube extends into the catheter sleeve cylindrical body through the small opening to provide aeration into the catheter sleeve, and the other end extends slidably through the small opening in the harness body.

8 Claims, 6 Drawing Sheets

EXTERNAL CATHETER

RELATED APPLICATIONS

This application claims the benefit of U.S. application Ser. No. 15/594,592 entitled "External Catheter" filed on 13 May 2017, the contents of which are incorporated herein by reference in its entirety.

COPYRIGHT NOTICE

A portion of the disclosure of this patent document may contain material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

Five million men suffer from incontinence in the United States alone. Servicing this clientele is a multi-billion-dollar business a year. Without an effective incontinence aid, this leaves these sufferers robbed of their dignity and ability to travel. Male incontinence is a serious health and lifestyle issue for millions of men worldwide. Current products are oppressively uncomfortable, and restrict blood flow because of clamps, are in effective, odiferous or undignified. Most are unreliable and incapable of supporting an active lifestyle, and prone to unacceptable amounts of leakage. Current methods are prone to irritation or infection for both internal catheters and condom catheters.

Controlling men's incontinence has always been an issue. Lack of full bladder control is an inconvenience that limits a person's ability to travel and participate in daily activities. Many different systems have been developed for the collection of urine. Various absorbent material such as the male diaper and pads are available on the market but are inadequate for lack of male bladder control. The male diaper is effective at collecting urine, but many problems result. The urine is in constant contact with scrotal tissue which causes irritation and possible infection. Furthermore, these absorbent devices are not reusable.

External catheters are an improvement in safety, economics, and ease of use, and are reusable. The existing art demonstrates that the collection of urine using an external catheter is fairly straightforward; however, satisfactory external catheters that do not leak, or cause infections because of moisture are hard to find.

An example of such a conventional catheter includes U.S. Pat. No. 4,022,213, issued to Stein on 10 May 1977, which teaches an external catheter that uses a tubular sleeve with an opening at one end for receiving a penis and a hose fitting outlet at the other end that is hooked up to a urine receptacle for receiving the urine. Stein's external catheter attaches to a jock strap, through an opening in the jock strap, and is affixed in place through corresponding openings mated by male and female snap fasteners. US Patent Application Pub. No. 2012/0165768 A1, issued to Sekiyama et al. on 28 Jun. 2012, teaches a similar male urine collector that is supported by a jock strap with an opening therethrough.

US Patent Application Pub. No. 2004/0176746 A1 issued to Forral on 9 Sep. 2004, teaches a urine collection system for males utilizing a flexible external catheter that is attachable to a jock strap device with an opening therethrough, and uses vacuum assistance which may include a squeeze bulb to create a vacuum but does not circulate air.

External catheters are designed to be one size fits all; however, the varying size of men's penises results in a catheter that is unusable by many men. The male penis varies significantly in size. Age, genetics, and previous history such as surgery has left many men with a much smaller penis. Using just one size catheter increases the problem of keeping a secure seal around the penis to prevent back flow of the urine.

U.S. Pat. No. 5,618,277, issued to Goulter on 8 Apr. 1997, shows a similar jock strap; and also, a useful valve and retaining means. International Publication No. WO 97/14353 published on 24 Apr. 1997 by Goulter teaches an external catheter with a jock strap holder with an opening therethrough, and the use of a condom-like material as an inner sheath around the male penis to limit leaking.

External condom catheter systems are used extensively by incontinent men. They are effective on collection of urine but remain in constant contact with the skin creating possible skin problems. Most use a glue to secure the catheter, and can be difficult to remove. Efforts have been made to increase air circulation. For example, US Patent Application Pub. No. 2006/0015082 A1, by Pearson et al. on 19 Jan. 2006, teaches having a plurality of openings in the side of the sheath in an effort to increase air circulation. Similarly, US Patent Application Publication No. 2015/0320583 A1 to Harvie on 12 Nov. 2015, teaches an air vented condom catheter that relies upon openings to allow air in towards the end of the catheter adjacent to the tubing. US Patent Application Publication No. 2013/0338617 A1 to Newton, Jr. on 19 Dec. 2013, teaches an external urinary catheter system that incorporates openings along the side of the sheath as air vents.

Recognizing the need for aeration, the prior art used holes or loose fitting attachments, which unfortunately allowed for leakage. This is particularly true when the wearer is sitting or reclining. Other designs did not provide for aeration, but this creates a wet, unhealthy environment inside the collection tube and as urine enters the unit, pressure and expansion are inevitable.

Many different sizes of collection bag are in use which range from 180 ml to 2000 ml. Many urine collection bags are attached to the penis which carries all of the weight. Different types of attachments are used to connect urine collection bags to the external catheter.

Previous art attempting to attach the penis to the body suffered from a serious flaw by utilizing modified underwear (brief or jock strap) with a waistband at the top of the garment attached around the waist. The jock strap and briefs are designed to allow freedom of movement of the male genitals. However, such freedom of movement is problematic for an external catheter as the penis is attached to the pelvic region, but the waist moves independently of the pelvic region; therefore, any twist or bend of the waist tends to pull the catheter away from the penis creating leakage.

Clearly, these known external catheters have several draw backs. The development of an external catheter that is effective, safe, economical, dependable, comfortable, easy to use, reusable, and works for everyone is desirable.

SUMMARY OF THE INVENTION

The present invention is an external catheter for a male. The external catheter has a harness to hold everything together. The harness has a cloth or mesh body with a belt strap, two leg straps, a small opening to slidably accommodate an aeration tube, and a larger opening to accommodate a catheter sleeve. The catheter sleeve has a length of cylindrical body which has a tapered end and a flexible end. The one end of the aeration tube extends into the catheter sleeve cylindrical body through the small opening to provide aeration into the catheter sleeve, and the other end extends slidably through the small opening in the harness body.

This external catheter provides either a passive or forced aeration around the penis which can reduce the possibility of irritation and infection. This unique feature allows a safer and more extended use.

The two ends of the belt strap are attached to the harness body on opposite sides of the catheter adjacent to the opening for the penis. This unique placement of the belt strap exerts equal and opposing force that prevents the movement of the catheter from the penis. The belt strap is distinguished from the waistband of the prior art in that it is more adjustable and for most users wraps around the body above the hips. This placement causes the catheter an up and inward force keeping the catheter in proper position. The two leg straps attached at the lower end of the belt strap of the harness to pull the catheter with a down and inward force. This combination prevents the penis being accidentally extracted from the catheter. These features allow a user to move without fear of dislodging the catheter.

The external catheter has a flexible seal and may be provided in various sizes to accommodate various sized members. The catheter, in different sizes, consists of a thin pliable condom-like material that can fit snugly around the penis to prevent urine leakage. The body of the catheter is larger than the penis to permit air circulation.

Further, the external catheter of the present design is reusable. The flexible end of the external catheter is the key item to prevent leakage, and as a unique feature of this design. The overall flexibility of the present invention helps prevent chaffing.

The external catheter of the present invention is comfortable and secure in use, and can accommodate most penis sizes or be scaled up and down to obtain the desired fit.

Yet another advantage of the present invention is that it's simple design prevents the catheter's position from becoming out of position or folded over increasing the chance of spilling or pooling of urine. The harness of the present invention secures the catheter to the pelvis thereby eliminating movement and the resulting leakage as the pelvis is static to the penis. The result is a harness that allows for considerable movement of the wearer without a shifting of the catheter away from the penis.

The harness as described herein is also superior to previous art using modified underwear in that the harness utilizes four straps which move independently of one another. Underwear, particularly garments with full back coverage, moves as the wearer moves or as parts of the body covered by the underwear comes into contact with objects which cause friction such as a chair. If one part of traditional underwear moves, such movement necessarily causes the rest of the garment to move with it, thereby displacing the penis from the catheter.

As the harness described herein utilizes four straps instead of full back coverage underwear, the movement of one strap will not greatly affect the other three straps, movement of the catheter will be minimal, and the catheter will remain in place on the penis. The placement of the straps and their elasticity allows the straps to move independently of one another and provides a counterbalancing force of the other straps that minimizes movement of the harness, keeps the catheter in place, and keeps the catheter secured to the penis.

The aeration tube provides two major advantages. First, it prevents the catheter from becoming air locked in place. The second advantage is that it provides air circulation about the penis to allow the inside of the catheter to be free of excess moisture. Any body movement creates an air exchange.

There are many advantages of this system over the prior art. Recognizing the need for aeration, the prior art used holes or loose fitting attachments, which unfortunately allowed for leakage. This is particularly true when the wearer is sitting or reclining. Other designs did not provide for aeration, but this creates a wet, unhealthy environment inside the collection tube and as urine enters the unit, pressure and expansion are inevitable.

The external catheter does not use glue, and is easy to put on and remove. It is just slid on and off as desired.

The flexibility of the external catheter of the present design has an advantage of being comfortable.

This external catheter is reusable. The external catheter may be readily cleaned with soap and water.

The design of the present external catheter is supported by the harness. The external catheter utilizes a one piece, flexible, through the harness design with a catheter sleeve narrows allowing for easy adjustment for penis size. The catheter is a one integral piece comprising a harness anchoring to the pelvis, noted above, with tube aeration (noted above) and features a highly flexible adjustable catheter sleeve and a collection tube.

The catheter sleeve allows for a leak free custom fit to each user regardless of the size of the penis with the use of highly flexible material on the inner sleeve. Some prior art has tried to avoid this problem with a clamp (irritating and highly uncomfortable) or glues which are difficult to remove or by avoiding the interior sleeve. The latter works acceptably until the wearer sits or reclines placing the collection tube higher that the wearer. Once this happens a form fitting interior sleeve is necessary to avoid the urine from back flowing through the harness opening.

These and other aspects of the present invention will become readily apparent upon further review of the following drawings and specification.

BRIEF DESCRIPTION OF THE DRAWINGS

The novel features of the described embodiments are specifically set forth in the appended claims; however, embodiments relating to the structure and process of making the present invention, may best be understood with reference to the following description and accompanying drawings.

DETAILED DESCRIPTION OF PREFERRED EMBODIMENTS

Figure 1:
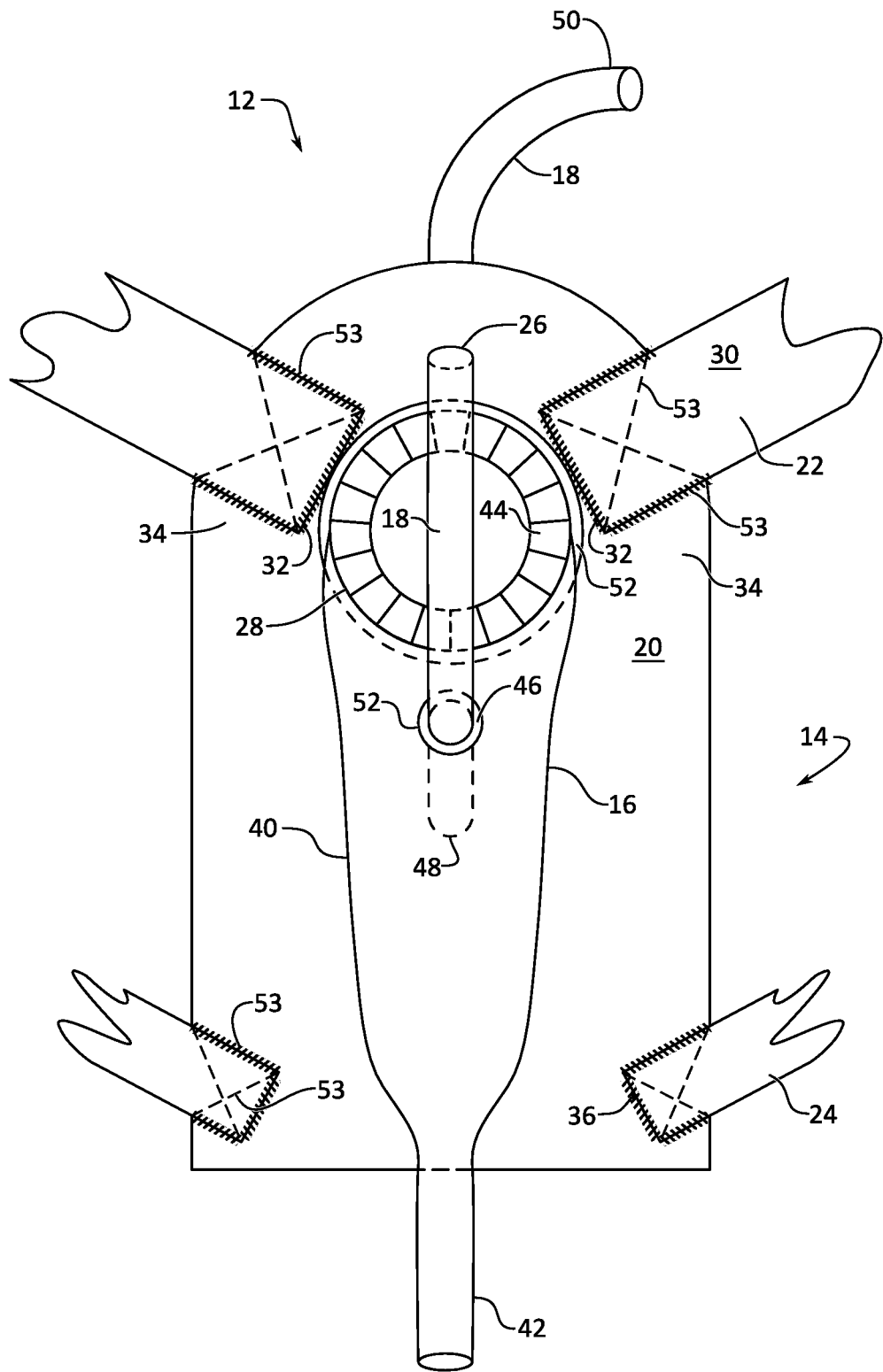
FIG. 1 shows a front view of an external catheter according to an embodiment of the present invention.
Figure 2:
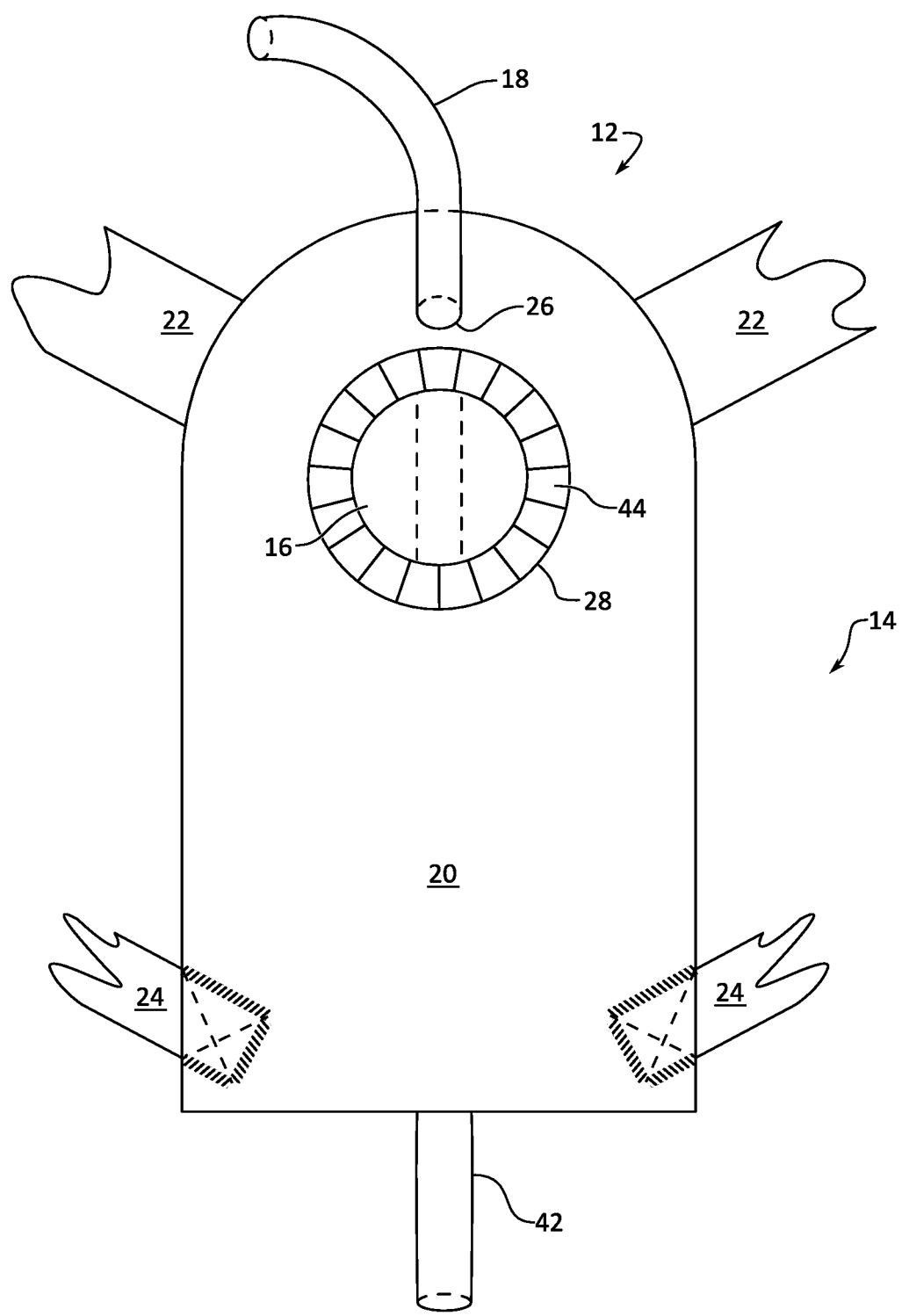
FIG. 2 shows a back view of an external catheter according to an embodiment of the present invention.
Figure 3:
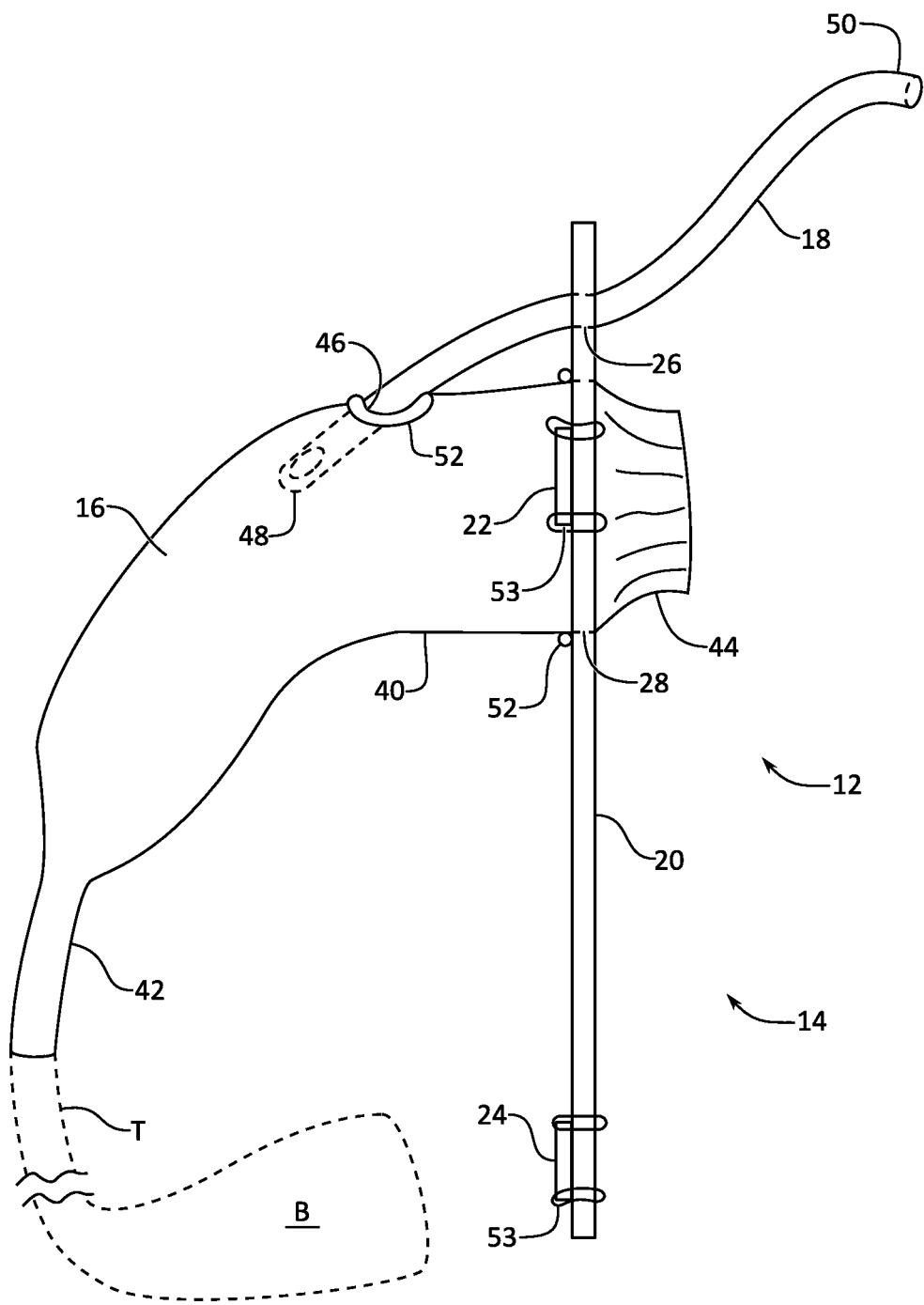
FIG. 3 shows a side view of an external catheter according to an embodiment of the present invention demonstrating the arrangement with an evacuation tube and collection bag attached thereto.
Figure 4:
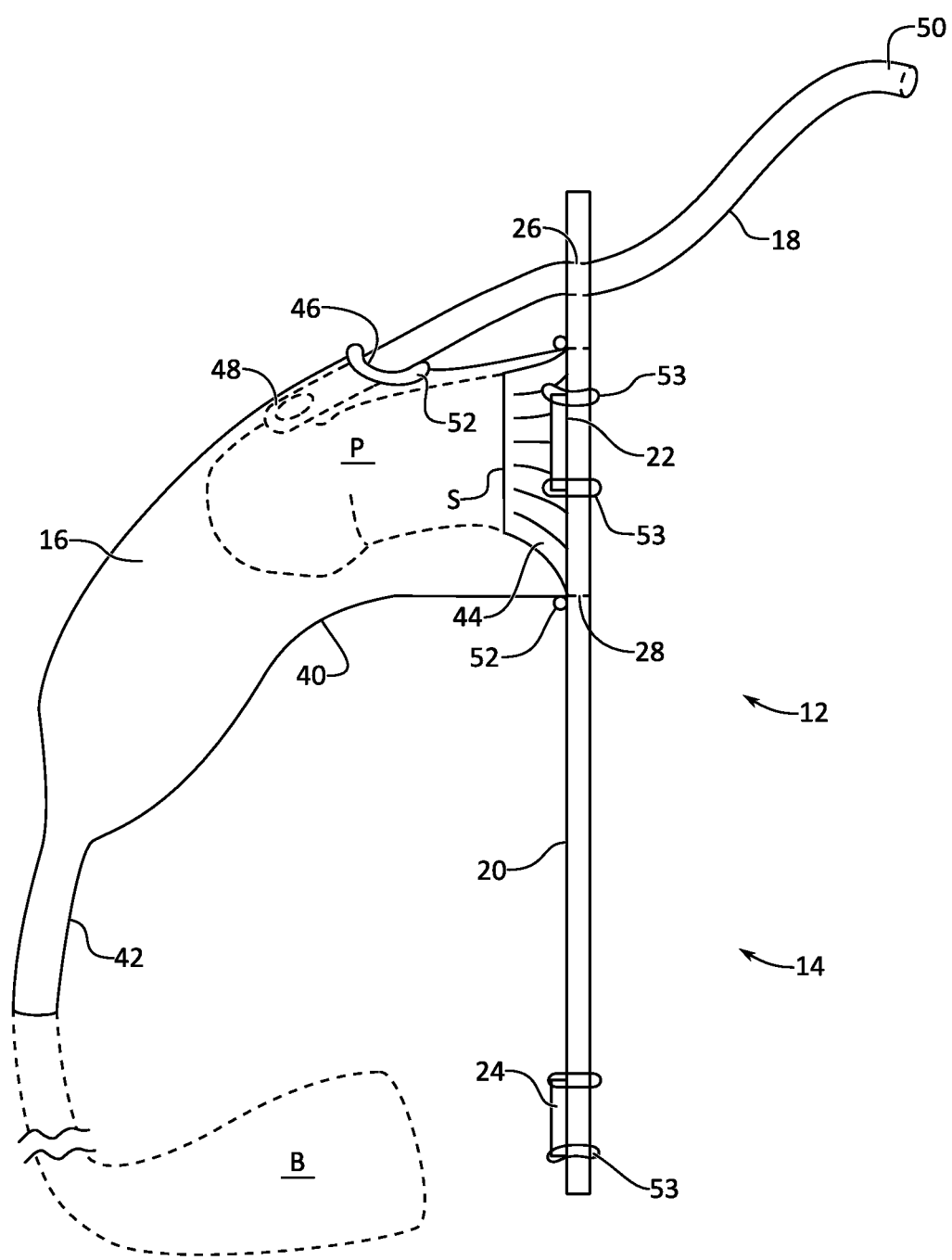
FIG. 4 shows a side view of an external catheter according to an embodiment of the present invention showing the arrangement when in use with a collection bag attached thereto.

An external catheter 12 for use by a male has a harness 14, a catheter sleeve 16, and an aeration tube 18 as shown in FIGS. 1 through 5. The harness 14 has a cloth or mesh body 20, a belt strap 22, two leg straps 24, and a small opening 26 to slidably accommodate the aeration tube 18 therethrough. The harness body 20 of the harness 14, shown from the front in FIG. 1 and the back in FIG. 2, has an opening 28 therethrough to accommodate the catheter sleeve 16. FIGS. 3 and 4 show the external catheter 12 from the side.

Figure 5:
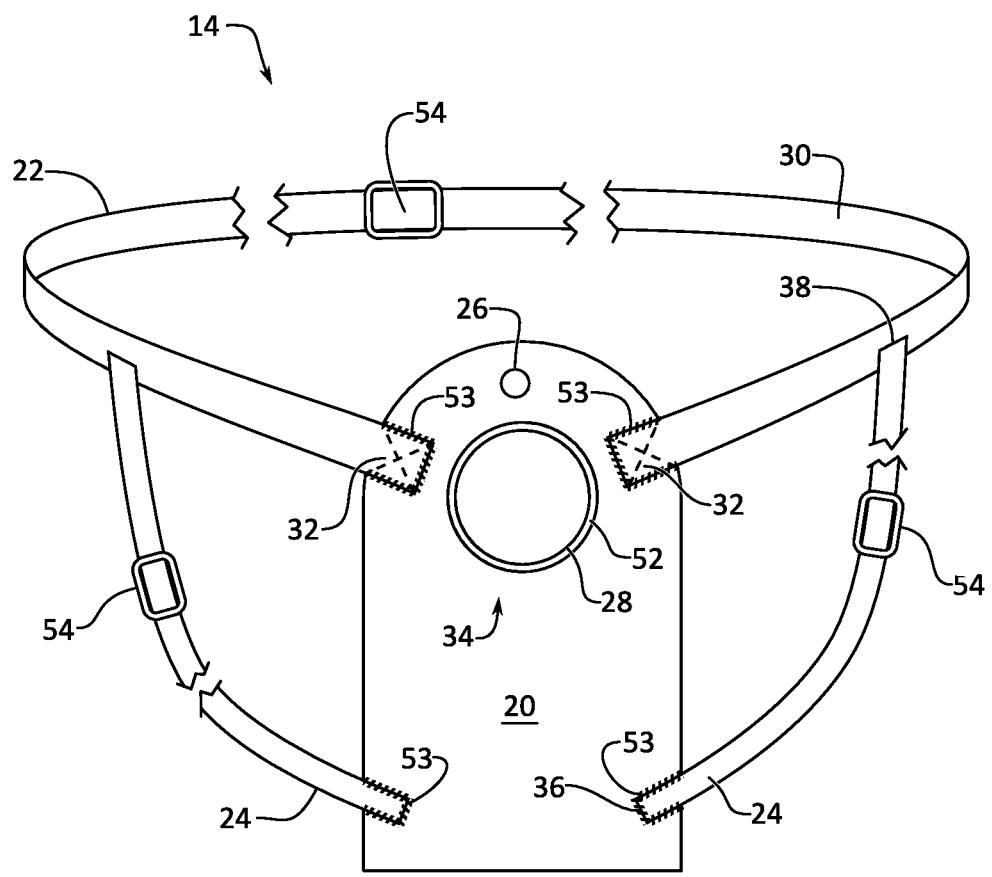
FIG. 5 is a front view of the harness which holds the external catheter in place showing the arrangement of belt strap and leg straps with adjustment means.

The belt strap 22, shown in FIG. 5, is composed of a length of strap 30 having two ends 32, and is attached to the harness body 20 at opposite sides 34 of the opening 28. Each of the two leg straps 24 has a first end 36 and second end 38, the first ends 36 of the leg straps 24 attach to the harness body 20 below the opening 28, and the second ends 38 of the leg straps 24 attach to opposite one another to the belt strap 22 adjacent the harness body 20.

The catheter sleeve 16 has a length of cylindrical body 40. The cylindrical body 40 has a tapered end 42 and a flexible end 44, and extends outward from the harness body 20 with the tapered end 42 open for attachment to a urine collection bag B, or evacuation tube T, to collect urine. Small bags, approximately twenty-five centimeters (25 cm) in the length with a capacity of one hundred eighty milliliters (180 ml), are convenient to use for the collection bag B but must be changed more frequently. Leg attached and overnight bags can vary in capacity from about six hundred (600 ml) and to about two thousand (2000 ml) milliliters. The ability to separate the urine bag, which is affected by our design, from the external catheter can be helpful. The evacuation tube T may be used between the catheter 12 and the collection bag B or similar collection receptacle (not shown). The flexible end 44 that flexibly extends from the opening 28 to provide a seal S about a penis P when in use. A small opening 46 is provided in the cylindrical body 40 to accommodate the aeration tube 18 therethrough.

The aeration tube 18 has first and second ends 48 and 50. The harness body 20 is attached to the catheter sleeve 16 about the cylindrical body 40 through the opening 28 in the harness body 20. The aeration tube 18 is attached to the catheter sleeve 16 cylindrical body 40 through the small opening 46 therein for the aeration tube 18, and extends slidably through the small opening 26 in the harness body 20, such that the first end 48 extends into the catheter sleeve 16 cylindrical body 40 and the second end 50 extends through the harness body 20 to provide aeration into the catheter sleeve 16. The aeration tube 18 is flexible ¼ inch silicon piping approximately 3 inches long. Once the external catheter is fitted to the wearer, the tube begins slightly above the penis and goes up, passing through the catheter wall and approximately 1½ inches upward. The tube is secured to keep it in place. This allows aeration inside the catheter with a very inexpensive mechanism which prevents leakage.

Different attachment methods and adhesives may be used such as silicone adhesive, glue, sewing, and the like. Alternatively, the pieces may be fused together. The various pieces are attached to each other with a silicone adhesive 52 and/or stitches 53. Stitches 53 may be used to securely attach the straps 22 and 24 to the harness body 20 and to each other. Furthermore, silicone adhesive 52 may be used to attach the catheter sleeve 16 to the opening 28 in the harness body 20 and the aeration tube 18 to the small opening 46 in the cylindrical body 40. Furthermore, many of the parts may be constructed all of one piece eliminating the need for adhesives.

The straps 22 and 24 may be composed of elastic or other resilient stretchy material. Adjustment means 54 may also be provided along the length of the strap 22 or 24 for adjusting the length thereof to create a more secure fit. The adjustment means 54 may include any conventional device for adjusting the length of a strap, including but no limited to buckles, hook and loop attachments, or the like.

The harness body 20 may be composed of cotton, or a cotton blend, but also may be made of other suitable flexible material, including nylon or other netting. The catheter sleeve 16 may be made of various materials including silicone.

Figure 6A:
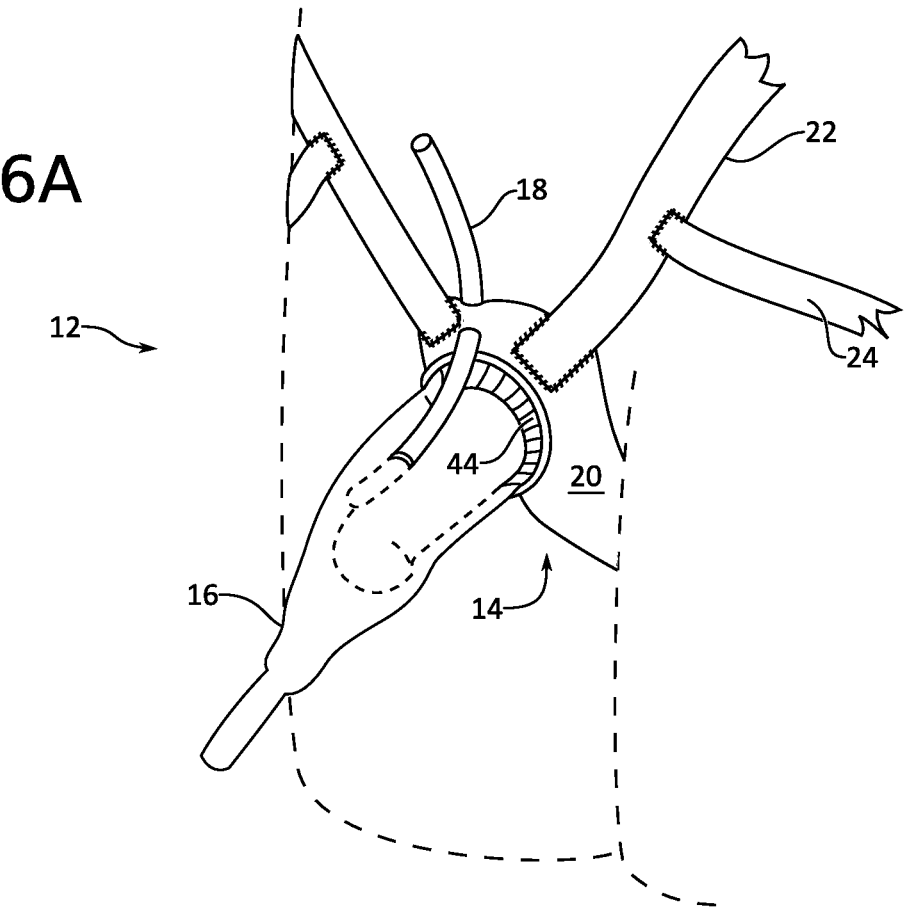
FIGS. 6A and 6B are environmental views of the external catheter as worn.
Figure 6B:
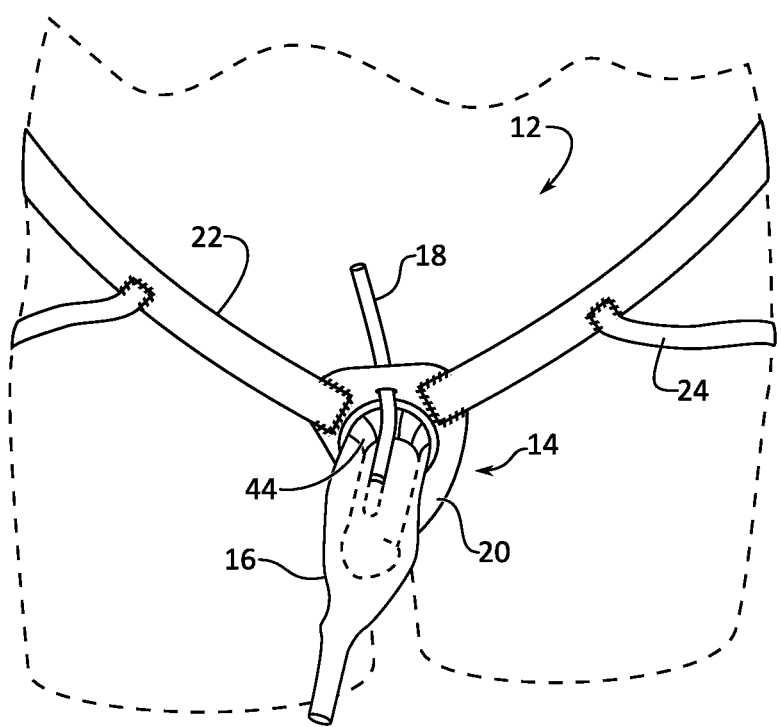

FIGS. 6A and 6B are environmental views of the external catheter as worn by a user. The external catheter 12 fits snuggly about the body and allows a fuller range of movement than other external catheters without the discomfort of gluing the product to the skin. The harness body 20 is secured by the belt straps at approximately 10:00 o'clock and 2:00 o'clock position, and by the leg straps at approximately 5:00 o'clock and 7:00 o'clock. By using four elastic straps that secure the catheter to the pelvis, the harness described herein gives a balanced and opposite force to counteract any movement of the wearer that would otherwise displace the penis from the catheter.

It is to be understood that the present invention is not limited to the embodiments described above, but encompasses any and all embodiments within the scope of the following claims.

What is claimed is:

1. An external catheter comprising:
a harness;
a catheter sleeve; and
an aeration tube having a catheter end and a harness end;
wherein the harness comprises:
   a harness body having a top edge, a bottom edge, and opposing side edges, the harness body further having:
     a first opening configured to engage the catheter sleeve; and
     a second opening located between the first opening and the top edge configured to accommodate the harness end of the aeration tube therethrough;
   a belt strap having two terminal ends attached directly to the harness body at opposite respective sides of the first opening, wherein a torso opening for receiving a torso of a user of the external catheter user is defined by the belt strap and the top edge of the harness body;
   two leg straps, each having a first end and a second end,
     wherein the first ends are attached to the belt strap proximate the harness body,
     wherein the second ends are attached to the harness body below the first opening and proximate the bottom edge, and
   two leg openings, each having a perimeter defined by the belt strap, one of the leg straps, and one of the opposing side edges of the harness body,
     wherein each leg opening is configured to receive a leg of the catheter user, and
     wherein the two leg straps are configured to be adjustable in length such that each of the perimeters of the leg openings may be decreased to secure each perimeter around each leg of the user;
wherein the catheter sleeve comprises:
  a length of cylindrical body,
    wherein the cylindrical body has a tapered end and a flexible end attached to the first opening,
    wherein the cylindrical body extends outward from the harness body with the tapered end open for attachment to a urine collection bag, or evacuation tube, to collect urine, and
    wherein the flexible end flexibly extends from the first opening to provide a seal about a penis extending therethrough;
  a third opening in the cylindrical body configured to accommodate the catheter end of the aeration tube therethrough;
wherein the aeration tube is attached to the third opening and the catheter end of the aeration tube extends through the third opening into the catheter sleeve, and wherein the harness end of the aeration tube extends slidably through the second opening such that the harness end remains above the top edge of the harness body, providing passive airflow to the catheter sleeve and preventing leakage of urine.

2. The external catheter of claim 1, wherein the belt strap is attached to the harness body by one of: an adhesive, stitches, or a combination thereof.

3. The external catheter of claim 1, wherein the leg straps are attached to the harness body by one of: an adhesive, stitches, or a combination thereof.

4. The external catheter of claim 1, wherein the leg straps are attached to the belt strap by one of: an adhesive, stitches, or a combination thereof.

5. The external catheter of claim 1, wherein the catheter tube is comprised of silicone.

6. The external catheter of claim 1, wherein the aeration tube is comprised of silicone.

7. The external catheter of claim 1, wherein the belt strap is configured to be adjustable in length.

8. The external catheter of claim 1, wherein the harness end of the aeration tube is configured to accommodate an aerator to provide forced aeration within the catheter sleeve.

\* \* \* \* \*